United States Patent
Wu et al.

(10) Patent No.: US 6,200,532 B1
(45) Date of Patent: Mar. 13, 2001

(54) DEVICES AND METHOD FOR PERFORMING BLOOD COAGULATION ASSAYS BY PIEZOELECTRIC SENSING

(75) Inventors: Jogin R. Wu, Durham; Mario Moreno, Raleigh, both of NC (US)

(73) Assignee: Akzo Nobel NV, Amhem (NL)

( * ) Notice: Subject to any disclaimer, the term of this patent is extended or adjusted under 35 U.S.C. 154(b) by 0 days.

(21) Appl. No.: 09/197,481

(22) Filed: Nov. 20, 1998

(51) Int. Cl.$^7$ .................................................. G01N 33/00
(52) U.S. Cl. .............................. 422/73; 436/69; 73/64.41; 73/64.42; 73/64.43
(58) Field of Search .................... 436/69; 422/73; 73/64.41, 64.42, 64.43

(56) References Cited

U.S. PATENT DOCUMENTS

| | | |
|---|---|---|
| 4,629,926 | 12/1986 | Siegal . |
| 5,026,348 | 6/1991 | Venegas ............................ 604/122 |
| 5,892,144 * | 4/1999 | Meller et al. ........................ 73/64.42 |

FOREIGN PATENT DOCUMENTS

| | | |
|---|---|---|
| 109239 | 11/1982 | (EP) . |
| 4032767 * | 5/1990 | (JP) . |
| 05/322736 | 5/1992 | (JP) . |
| WO 9809139 | 8/1996 | (WO) . |

* cited by examiner

*Primary Examiner*—David A. Redding
(74) *Attorney, Agent, or Firm*—Gregory R. Muir

(57) ABSTRACT

A device and method for performing blood coagulation assays, particularly prothrombin times and activated partial thromboplastin times and other clotting parameters are disclosed. The device comprises a disposable strip (containing a sample inlet for sample delivery, a capillary channel for driving force, and a reaction chamber with an appropriate dry reagent for a specific assay) and a piezoelectric sensor. The device could also include a heating element for temperature control, and a magnetic bender. The magnetic bender is driven by an electromagnetic field generator and is attached onto a piezoelectric film in contact with the blood sample. Electric signal generated at the piezo film is characterized by its frequency and amplitude due to the movement of the attached metal film. The signal collected at the site of the piezo film represents the process of a biochemical reaction in the reaction chamber, while blood sample proceeds to the point at which clot formation starts and is amplified by an amplifier and rectified into a Dc voltage and is sent to a recording unit and/or display unit.

33 Claims, 14 Drawing Sheets

DEVICES AND METHOD FOR PERFORMING BLOOD COAGULATION ASSAYS BY PIEZOELECTRIC SENSING

BACKGROUND OF THE INVENTION

1. Field of the Invention

The present invention relates to a device and method for performing blood coagulation assays, particularly prothrombin times; activated partial thromboplastin times and other clotting tests. It also relates to a portable device that is easy is to use, accurate and rapid for routine testing at a patient's bedside, physician's office, operating room, or even at a patient's home for patients under anticoagulant therapy. The invention comprises a disposable test strip, and a piezoelectric sensor for detecting signals collected as the sample proceeds to clot formation.

Blood clotting is a result of a series of biochemical reactions where fibrinogen turns into cross-linked polymeric fibrin through several enzymatic reactions (known as the extrinsic and intrinsic coagulation pathways). Determination of coagulation parameters, such as prothrombin time (PT) and activated partial thromboplastin time (APTT) and other coagulation parameters has a large impact on the cure and prevention of thrombolic and/or fibrinolytic abnormalities.

Point-of-care testing uses advances in technology to improve turn-around-time. New point-of-care technologies based on miniaturized whole blood biosensors allow results to be obtained at the hospital bedside in minutes with accuracy and precision equivalent to that provided by the central clinical laboratory. The advent of these technologies, and the demands of physicians for more timely diagnostic test results in order to facilitate the patient management process, has resulted in rapid growth of this specific clinical testing segment.

Point-of-care testing provides health care quickly, effectively, and efficiently to the patient at the time and in the manner that it does the most good. It extends across the entire health care spectrum, from early diagnosis and timely institution of therapeutic measures during a visit in a doctor's office to optimizing critical care in a tertiary hospital setting and close monitoring and rapid intervention in an intensive care unit (ICU). It also provides cost-effective health care by maximizing the efficacy and efficiency of the providers.

Data from extensive experience with self-testing demonstrates that increasing the frequency of prothrombin time (PT) testing in turn increases a patient's time within therapeutic range. In order to reduce thromboembolic complications at both ends of the coagulation spectrum, tight control of a patient's PT (INR) is essential. It has been estimated that 40,000 strokes could be avoided each year if warfarin were prescribed for arterial fibrillation patients. Warfarin is used in long-term anticoagulation therapy. Almost 2 million Americans take either heparin or warfarin for as long as they live after having a cardiovascular incident or disease. Most warfarin users have experienced aterial fibrillation, are at risk for deep vein thrombosis, or have recently had a stroke or transmural myocardial infarction.

Clinical studies have indicated that self-testing may improve patient treatment over the current method of monitoring anticoagulation therapy. Studies have shown that patients who self-monitor their anticoagulant drug usage are within the correct therapeutic range 80%–90% of the time, versus 60%–70% when monitored by an anticoagulant management service or a physician. Point-of-care instrumentation also provides speedy, on-site analysis that can be used in hospital operating rooms to monitor the effectiveness of drugs administered to prevent or dissolve blood clots.

Lack of accuracy and precision, difficulty of doing quality control and higher cost per test has resulted in a less rapid development than had been predicted for point-of-care products. An accurate, yet precise and reliable point-of-care device is needed for ease of use, efficiency, simplicity and compatibility with automated laboratory instrumentation.

2. Related Art

U.S. Pat. Nos. 5,110,727 and 4,849,340, to Oberhardt relates to a commercial point-of-care system TAS (Thrombolytic Assessment System). The TAS system uses paramagnetic iron oxide particles (PIOP)/dry chemistry technology. It is based on near-infrared sensing of the motion of PIOP contained in a dry reagent, situated as a film on the surface of a flat-capillary reaction chamber mounted on a plastic test card. The PIOP are subjected to an oscillating magnetic field generated by the instrument in which the test card is placed. When blood or plasma is added to a sample well of the test card, the sample enters the reaction chamber, reconstituting the reagent and freeing the PIOP so that they can move in response to changes in the magnetic field with time. The PIOP motion changes when an in vitro thrombus forms. This change results from PIOP entrapment during fibrin polymerization or release during fibrinolysis, providing a kinetic response curve, from which the analyzer determines clotting time and a parameter characterizing fibrinolysis process.

U.S. Pat. No. 3,695,842, to Minz, assigned to International Technydyne Corporation has a precision magnet in a reagent-containing test tube. When the test tube is filled with sample and inserted in a test well containing a magnetic detector, the tube slowly rotates. When the clot begins to form a change in the position of the magnet is detected.

A second patent assigned to International Technydyne Corporation (U.S. Pat. No. 5,372,946) discloses a disposable cuvette within which is formed a capillary conduit having at least one restricted region. The blood is forced to flow through the restricted region back and forth within a test channel. Two photo-optical detectors are used to measure the speed of sample movement.

U.S. Pat. No. 4,756,884 discloses a technology developed by Biotrack based on optical measurement of a speckle pattern from cells or particles from a sample illuminated by coherent light and flowing in a long capillary track of a plastic reagent-containing cartridge. When clotting occurs, the speckle pattern measurement indicates cessation of flow in the capillary track.

U.S. Pat. No. 4,599,219 assigned to Hemotec discloses a cylindrical plastic cartridge with a plunger assembly terminating in a "flag" at one end and a "daisy" at the other end. The plunger, situated in a reaction chamber above a reagent chamber, is moved by an external mechanical actuator. Flag movement through the clot reaction chamber is timed by a photo-optical detector, the end point being established when fibrin forms on the daisy and slows the plunger movement.

U.S. Pat. No. 5,167,145 describes a technology using infrared electromagnetic energy. Infrared electromagnetic transmission changes through a sample from a source of infrared energy to suitable detection electronics producing a peak signal representing the clotting time.

U.S. Pat. No. 5,601,995 to Exner and assigned to Gradipore Limited, Australia discloses a method where a blood sample is applied to a porous sheet and at least one of a spreading extent and a spreading rate are measured by either an optical property, or an electrical potential across the porous sheet to determine the propensity of the sample to coagulate.

U.S. Pat. No. 5,418,143 to Zweig and assigned to Avocet Medical Incorporated, Los Gatos Calif., is directed to a method for detecting clot formation in whole blood sample. A test strip is disclosed which comprises a porous membrane having a coagulation initiator and a substate impregnated therein. The substrate is activated by thrombin and produces a detectable fluorescent signal as the output.

Though the above technologies could be considered to be useful in a "point-of-care" environment, these technologies are either complex to build and/or use, or lack reproducibility and/or precision. Often, a very complicated multi-parameter optimization process has to take place to meet basic specifications for point-of-care use. In order to be effective, a device should be simple, be minimally parameter dependent, ease detection and be robust.

SUMMARY OF THE INVENTION

It is an object of the present invention to provide a simple, easy to use, portable device which can be used in point-of-care settings (such as a physician's office, an emergency room, at the patient's bedside and/or at the patient's home when routine monitoring is needed for the patient under therapy).

It is a further object of the present invention to provide a device for performing blood coagulation assays to assess a patient's hemostasis/thrombosis state, particularly but not limited to prothrombin times (PT) and activated partial thromboplastin times (APTT). Other coagulation parameters such as International Normalized Ratio (INR), Hypercoagulable and Hypocoagulable State, and Clot-based Low Molecular Weight Heparin assays are additional tests that can be performed on the device, among others.

It is another object of the present invention to provide methods characterizing coagulation parameters of a sample by creating mechanical vibration with a bender made of a thin iron film attached to a piezoelectric element. Variations in the bender movement are detected by a piezoelectric element that provides a signal corresponding to the time required for the formation of a fibrin clot. An electric circuit is provided to collect signal generated at the piezoelectric element; and a differential amplifier is provided to enhance the signal obtained at the piezoelectric film surface in contact with a whole blood specimen.

It is still a further object of the present invention to provide a mechanism for separating red blood cells from whole blood in case a plasma sample is desired, and to provide such a separation mechanism as part of a point-of-care device.

It is still another object of the present invention to provide a mechanism for compensating for the effect of the different hematocrit content in a patient's whole blood sample in a device for measuring one or more coagulation parameters of interest.

It is still another object of the present invention to provide a housing which forms an enclosed test strip comprising an air reservoir as the source of capillary force, and for providing such a housing with air reservoir as part of a point-of-care test device.

The above and other objects of the present invention are achieved by providing a test strip comprised of a sampling inlet and capillary channel, a reagent well containing appropriate dried reagent for the specific coagulation parameter of interest; a dual channel for sample control, a metal film and a piezo film.

The present invention also provides a variety of techniques for generating and detecting piezoelectric signal related to coagulation parameters as described in detail below in the drawings, examples/embodiments, and appended claims.

DETAILED DESCRIPTION OF THE PREFERRED EMBODIMENT

The viscosity of a blood sample, either whole blood or plasma, changes upon clot formation due to the formation of cross-linked polymeric fibrin. In the present invention, a piezoelectric film is used, such as lead-zirconate-titanate (PZT), $BaTiO_3$, lead-magnesium-niobate (PMN), or preferably polyvinylidene fluoride (PVDF). A better-preferred film is a PVDF film with a low Q value (high damping) and low attenuation in a water-like liquid. The piezo element will change its characteristics upon the formation of a clot in a sample, e.g. blood or plasma. The signal collected at the piezo element, as a function of time, will be an indicator of the changed characteristic, in this case blood coagulation.

Figure 1:
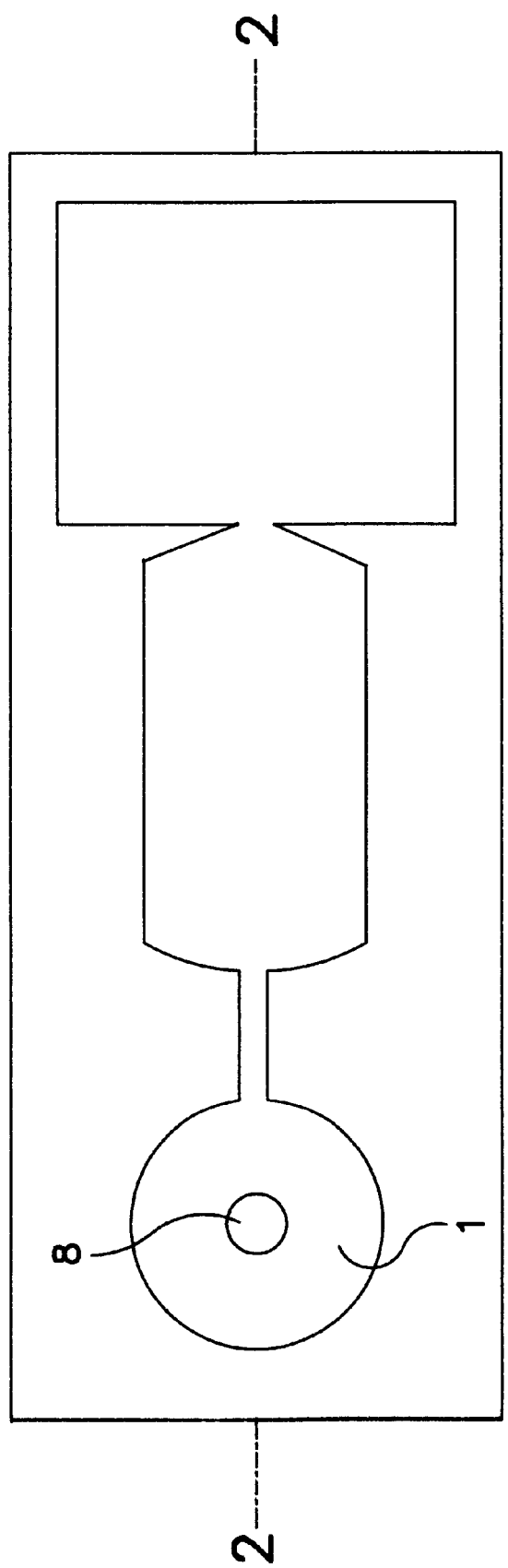
FIG. 1 is an illustration of a reaction chamber of one embodiment of the test device.
Figure 2:
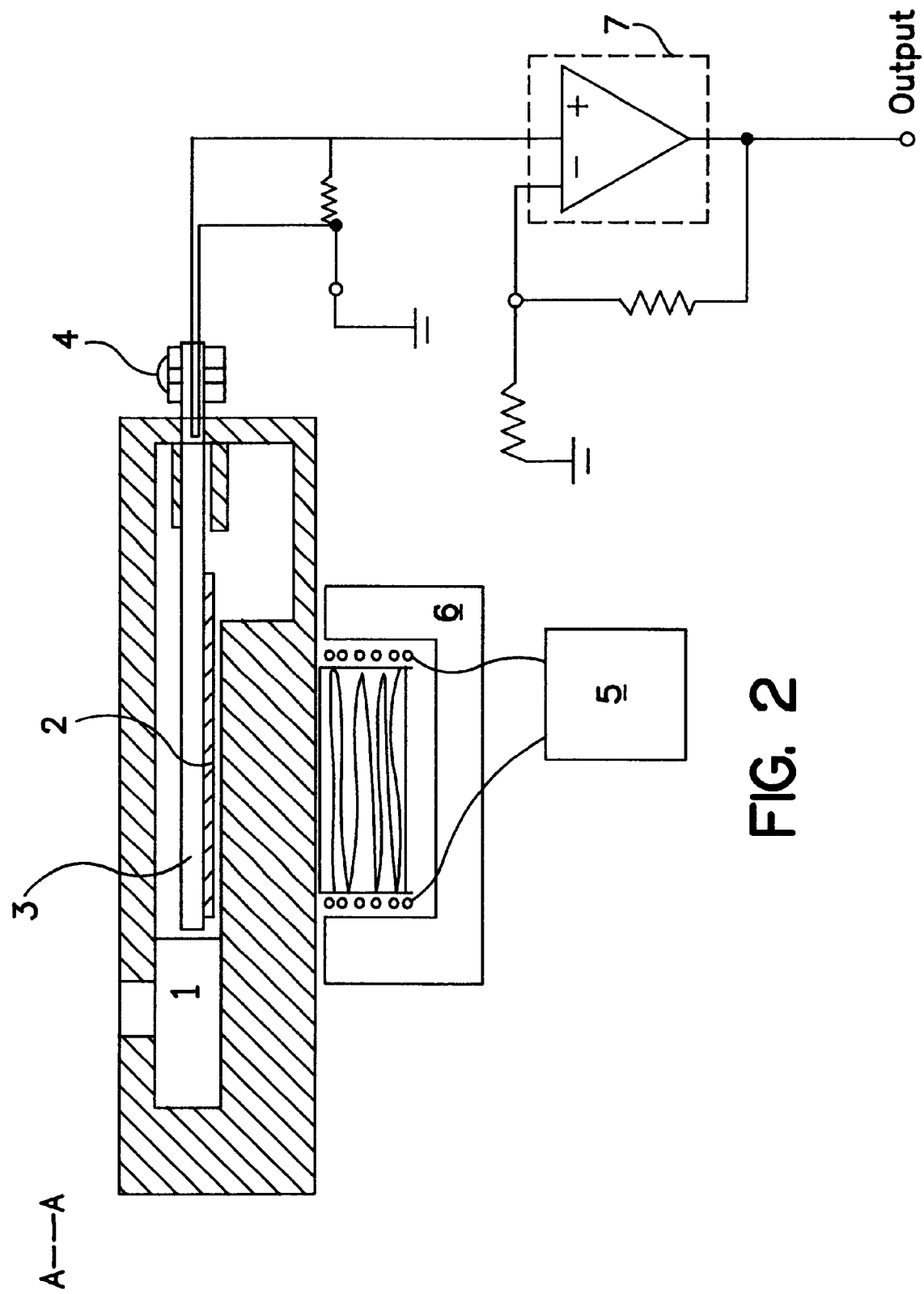
FIG. 2 is a cross sectional view taken along line A—A of FIG. 1.
Figure 3:
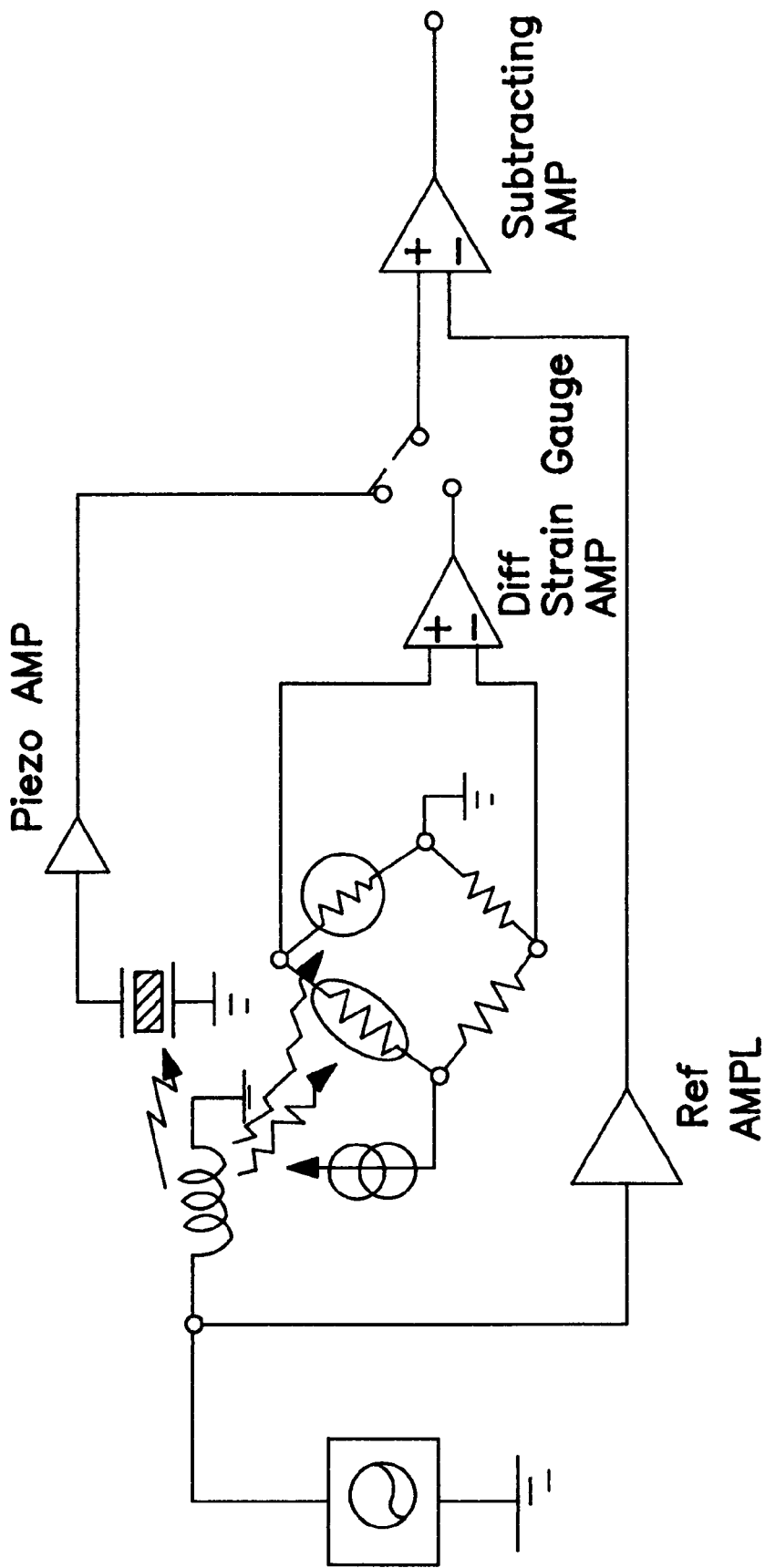
FIG. 3 is an example of a detection circuit for the present invention.

FIGS. 1 and 2 are views of one embodiment of the invention. Whole blood sample can be delivered to a reaction well 1 in a plastic strip (see FIG. 4 for details of the strip) via a sample- receiving aperture 8. A magnetic bender 2 is provided, which can be made of an iron-based material (such as alnico, ferrite etc.), and is attached to the piezoelectric film 3. The piezoelectric film is supported by a rigid support 4 at one end thereof. An electronic circuit 7 is connected to the piezoelectric film for signal amplification. On a side of the reaction chamber opposite to the piezoelectric film is an AC excitation generator coil 5 that produces an Ac electromagnetic field which drives an iron-based magnetic bender to vibrate and an E-type electromagnet 6 provides a constant electromagnetic field. After adding a blood or plasma sample, the sample in the sample channel is mixed with an appropriate reagent (e.g. Simplastin HTF for PT) via the vibration of the magnetic bender. (The reagent can be added with the blood or plasma sample, or can be already present in the device.) The sample proceeds towards clot formation after mixing with the reagent. An electromagnetic field is generated by an electro-magnet with a frequency of 1 to 100 kHz (preferably 10 to 50 kHz, e.g. 32 kHz) with a high power "E" frame transformer. Magnetic bender 2 vibrates under the electro-magnetic field variations. Electric signal is generated at the piezo film characterized by its frequency and amplitude due to movement of the attached metal film. The amplitude signal changes while the blood or plasma sample proceeds to clot formation. A changing point is observed once the clot formation begins (clotting time). The amplitude of the piezoelectric signal starts to change when clot formation is initiated. FIG. 3 shows the electronic circuit for the piezoelectric unit and its amplifier and rectifier. A data manipulation algorithm can be applied to the collected signal giving a clinically relevant value of clot formation (e.g. prothrombin time, activated partial thromboplastin time etc.) and is displayed as a result on an LCD panel.

EXAMPLE 1

A device is provided as shown in FIG. 2. An electromagnet 5 is located underneath the test strip with a high power "E" frame transformer. An electromagnetic field is generated at a frequency of 32 kHz. A magnetic bender 2 is made of a Ferrite film having a thickness of 250 $\mu$m. A piezo film made of PVDF (purchased from Atochem Sensor, Inc., Valley Forge, Pa.) having a thickness of 110 $\mu$m, is attached to the magnetic bender. Through the attachment of the piezo film to the magnetic bender, mechanical stress and movement at the piezo film generates an electric signal. 200 $\mu$l of liquid Thromboplastin Excel S reagent, a reagent for prothrombin time determination (obtained from Organon Teknika Corporation, Durham, N.C.), is provided on the test strip (in the reaction chamber 1) and lyophilized overnight. Another strip is made with no reagent (control strip). A 300 $\mu$l plasma sample was delivered onto the sample well in the test strip for both sample strip and control strip. A timer was triggered at the time the sample is delivered and an electric signal was recorded by a chart recorder (as well as a precision digital potentiometer) in the units of millivolts. For the control strip (with no reagent) a constant signal of 2100 mV is observed. For the sample strip the detected signal remains at a substantially constant value at 2100 mV for 55 seconds (the test strip being at room temperature) until a time at which a sudden change in electric signal occurs (1600 mV). At this point the sample begins clot formation. Compared with the control (plasma sample without reagent) a total of 23.8% change in signal intensity occurs due to clot formation. The noise level in this experiment was 0.5 mv, so that a signal-to-noise ratio of 1000:1 was achieved. In another experiment where sample was delivered into a lyophilized reagent cell maintained at 37° C., clot formation started after 13 seconds.

Figure 4:
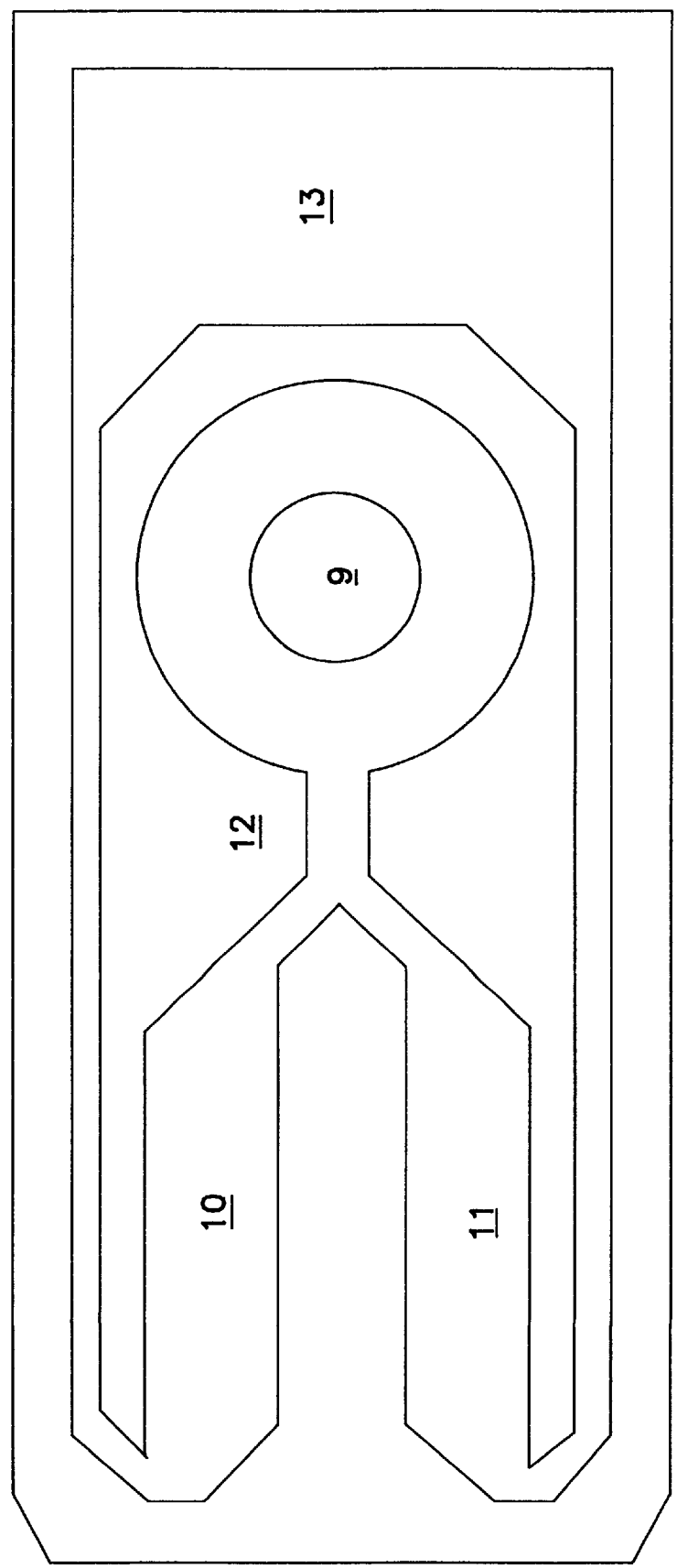
FIG. 4 is an illustration of a reaction chamber of another embodiment of the invention.

FIG. 4 is a plain diagram of the test strip. The strip is made of a polyester thin film with thickness of 0.01" and spacer thickness of 0.005". Sample inlet 9 allows whole blood sample to be delivered onto the plastic strip. The blood sample moves into the channel due to capillary force. Reaction chamber 10 contains an appropriate reagent (e.g. Simplastin HTF for PT) either in lyophilized form or air-dried form. A control channel has the exact geometry and dimensions as the reaction chamber, except that there is no reagent therein. The air reservoir has a much greater depth compared with the sample chambers (reaction and control chambers can be 0.005" in thickness) and capillary force is generated as soon as a sample is delivered onto the strip and air (in the air reservoir) is compressed. Whole blood samples from different individuals have different hematocrit content and could be different from anywhere between 35 to 70%. Samples with different hematocrit content have different viscosity. Since the control chamber has exactly the same geometry as the reaction (except no reagent) piezoelectric response from two channels is compensated and difference signal is collected and amplified through the use of piezo amplifier and differential amplifier. Thus only the signal which relates to the clot formation process is differentiated and being amplified.

Figure 5:
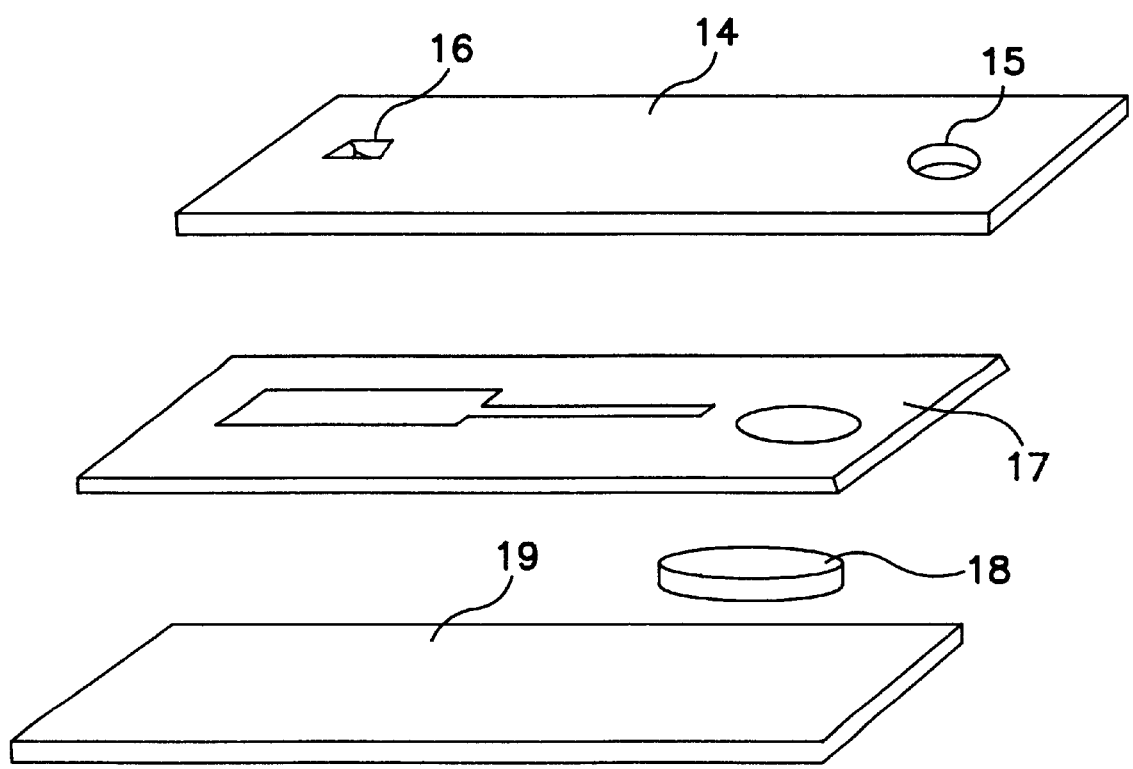
FIG. 5 is an illustration of the reaction chamber of the invention having an asymmetric membrane for single membrane separation of whole blood.

Another way of making prothrombin time measurements independent of hematocrit content is to separate red blood cells from the whole blood sample. This separation can be realized by using, for example, a polysulfonate asymmetric membrane and the capillary effect of sample channeling. FIG. 5 shows the geometry of this feature. The top layer can have, for example, a thickness of 0.010" and an inlet 15 for sample delivery. An air venting hole 16 can also be made part of the device as shown in FIG. 5. Middle layer 17 can be 0.005" in thickness and have adhesives on both surfaces assembling ease. A channel (e.g. of 0.009" in width) forms a capillary and reaction chamber (the reaction chamber can be 0.5×1.5" in size containing dried reagent). The polysulfonate asymmetric membrane 18 is placed between middle layer 17 and bottom layer 19 and is constructed very tightly so that a capillary force is generated after liquid flow through the membrane. Plasma is filtered out and flows into the reaction chamber through the capillary channel. This embodiment can be used wherever a plasma sample is desired for particular coagulation assays.

EXAMPLE 2

A test strip is constructed for applications where a plasma sample is desired for use. Such a strip can be made of three layers of polyester film (3M, Inc., St. Paul, Minn.). The top and bottom layers are made with a thickness of 0.010 in. and the middle layer is a double-coated adhesive film having a thickness of 0.005 in. (Scotch™ 467 MP or 468 MP High Performance Adhesive, 3M Inc. St. Paul, Minn.). A 0.05 inch in. diameter, 0.005 in. in depth and 1.500 in. in long (capillary channel is constructed as shown in FIG. 5. An asymmetric polysulfonate membrane 18 as shown in FIG. 5, is provided, having 127 $\mu$m thickness and 0.5 in. diameter (Primecare Inc. the Netherlands), and is placed between the middle and bottom layer of the plastic strip. 70 $\mu$l of whole blood sample is delivered onto the top sample inlet 15 as shown in FIG. 5, and after 15 seconds, a total of 30 $\mu$l of plasma is obtained at the reaction chamber. Another type of asymmetric membrane that could be used is from Memtec (BTS Asymmetric Polysulfone membrane with 20 $\mu$m in pore size on one end and 0.1 $\mu$m in pore size on the other end and 125 $\mu$m in thickness—Memtec, San Diego, Calif.). A 15 seconds separation time is achieved for 70 $\mu$l of whole blood sample.

Figure 6:
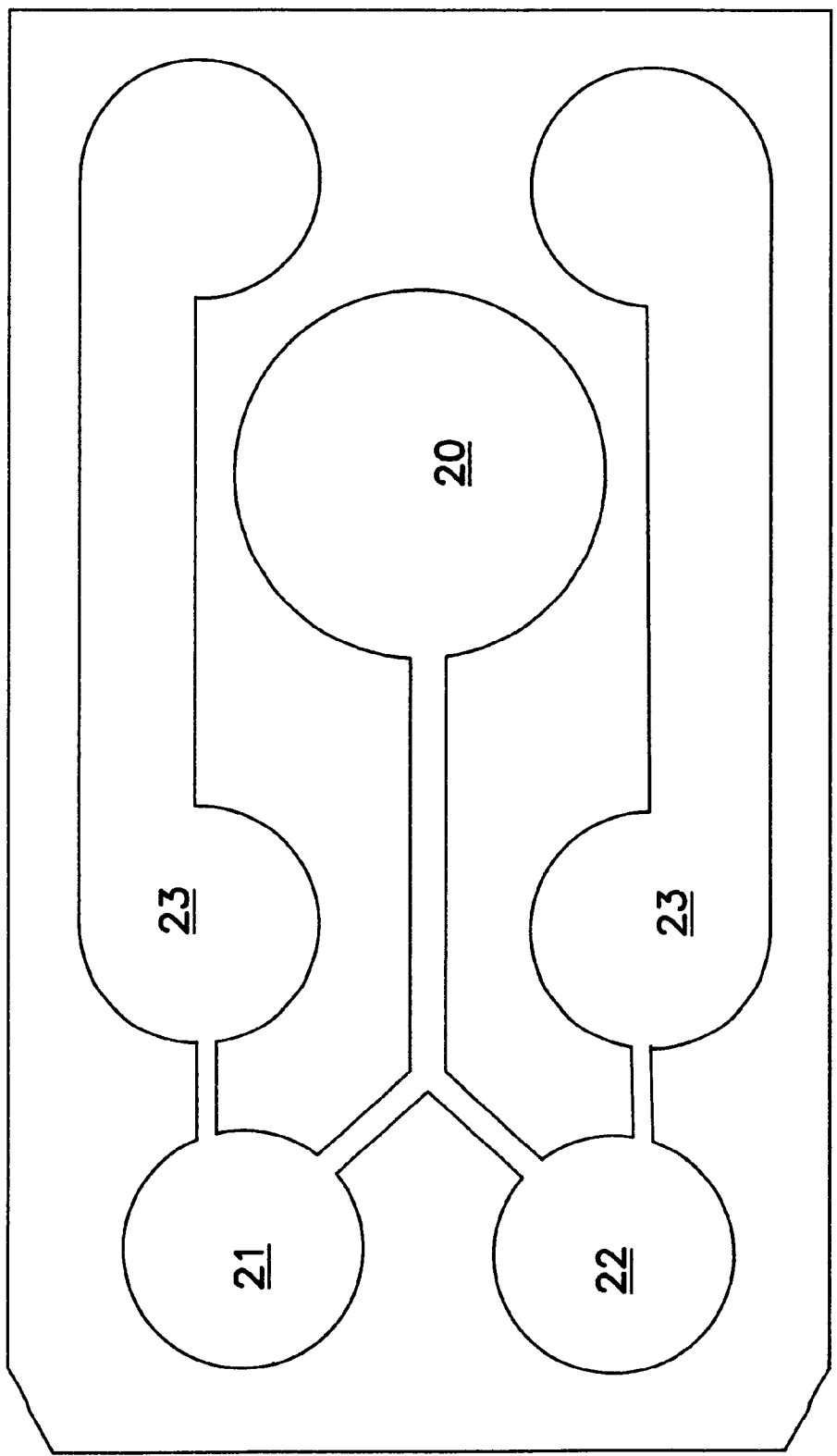
FIG. 6 shows a reaction chamber of another embodiment of the invention, having dual channel compensation and an air reservoir.

FIG. 6 illustrates another embodiment of this invention. Sample inlet 20 is designed for whole blood sample delivery. Element 21 in FIG. 6 is the reaction chamber, while element 22 is the control chamber. Both sides of the chambers have an air reservoir as the compensation utility.

FORCE SENSOR SENSING

Figure 7A:
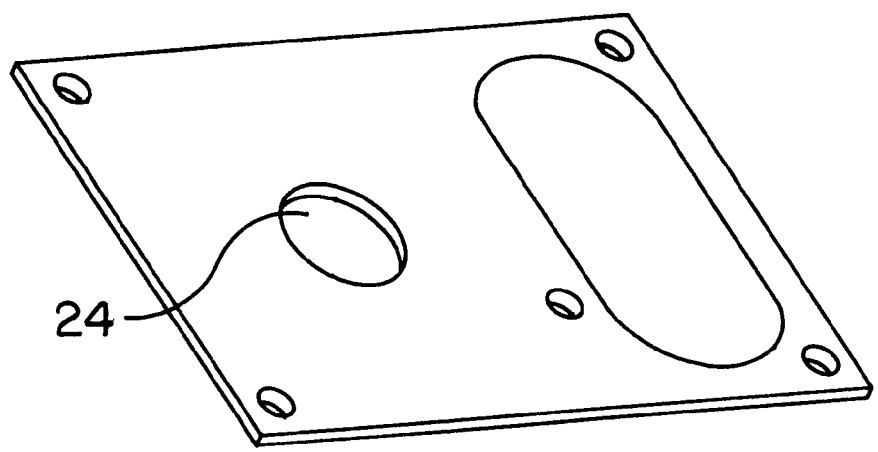
FIGS. 7a and 7b are illustrations of a spiral channel cover plate and a dual spiral channel plate.
Figure 7B:
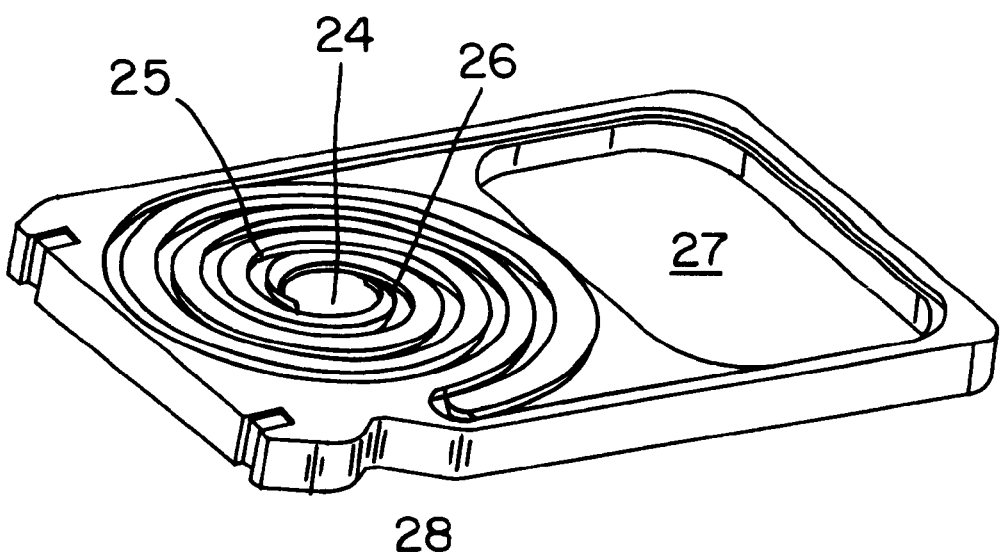

FIGS. 7a and 7b illustrate further features of the invention, where a dual spiral cassette is used to form two-channels in order to compensate different hematocrit effect. Multiple sensing may be incorporated as will be discussed below. FIG. 7b shows a top layer of the strip where element 24 is the sample inlet. FIG. 7a illustrates the reaction chamber 25 and the control flow chamber 26, which are essentially two spiral channels twisted in a way that sample flows into the two simultaneously by capillary force (driven by compressed air in the air reservoir 27). The reaction chamber contains reagent while the control chamber has no reagent.

Figure 8:
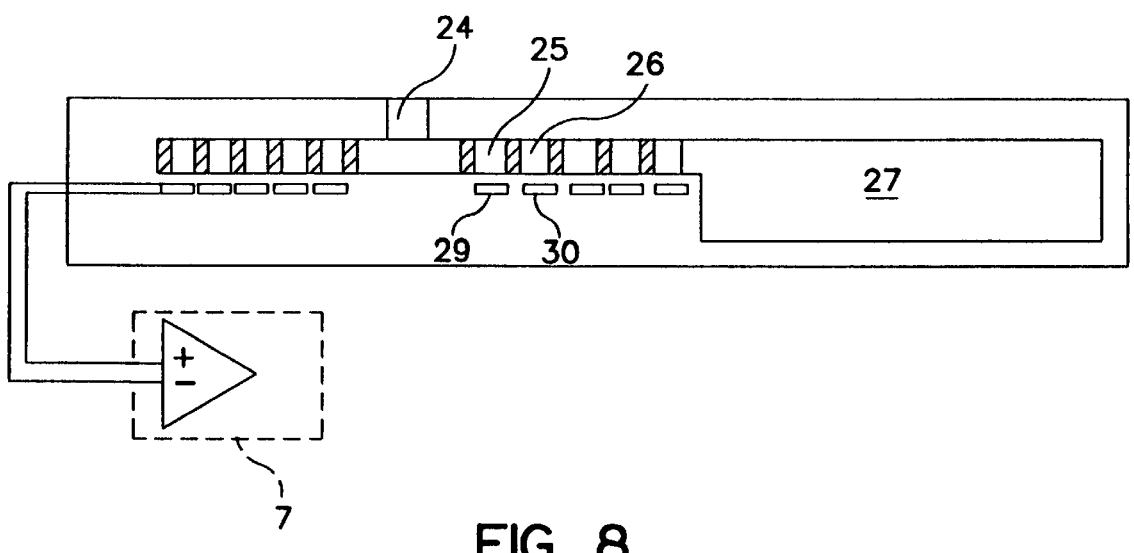
FIG. 8 is a cross sectional view of a spiral channel and piezoelectric sensing unit within an air reservoir.

FIG. 8 is a sectional view which includes a cross sectional view of FIG. 7b. Illustrated are sample inlet 24, spiral channels 25 and 26, air reservoir 27. Also shown are two piezosensing units 29 and 30 underneath each channel of spiral. The force sensor (e.g. a PVDF film) located at the bottom of the spiral are connected with electronic circuit and piezo amplifier. When fluid sample flows into spiral channel driven by capillary force the air in the reservoir chamber is compressed and the force sensor film experiences a pressure. When fluid in the reaction chamber proceeds to clot formation a signal on the force sensor is detected as differentiated with the control channel that has no reagent. A differential amplifier 30 amplifies this signal and defines the clot formation (prothrombin time in the case of using thromboplastin reagent).

ULTRASONIC ATTENUATION

Figure 9:
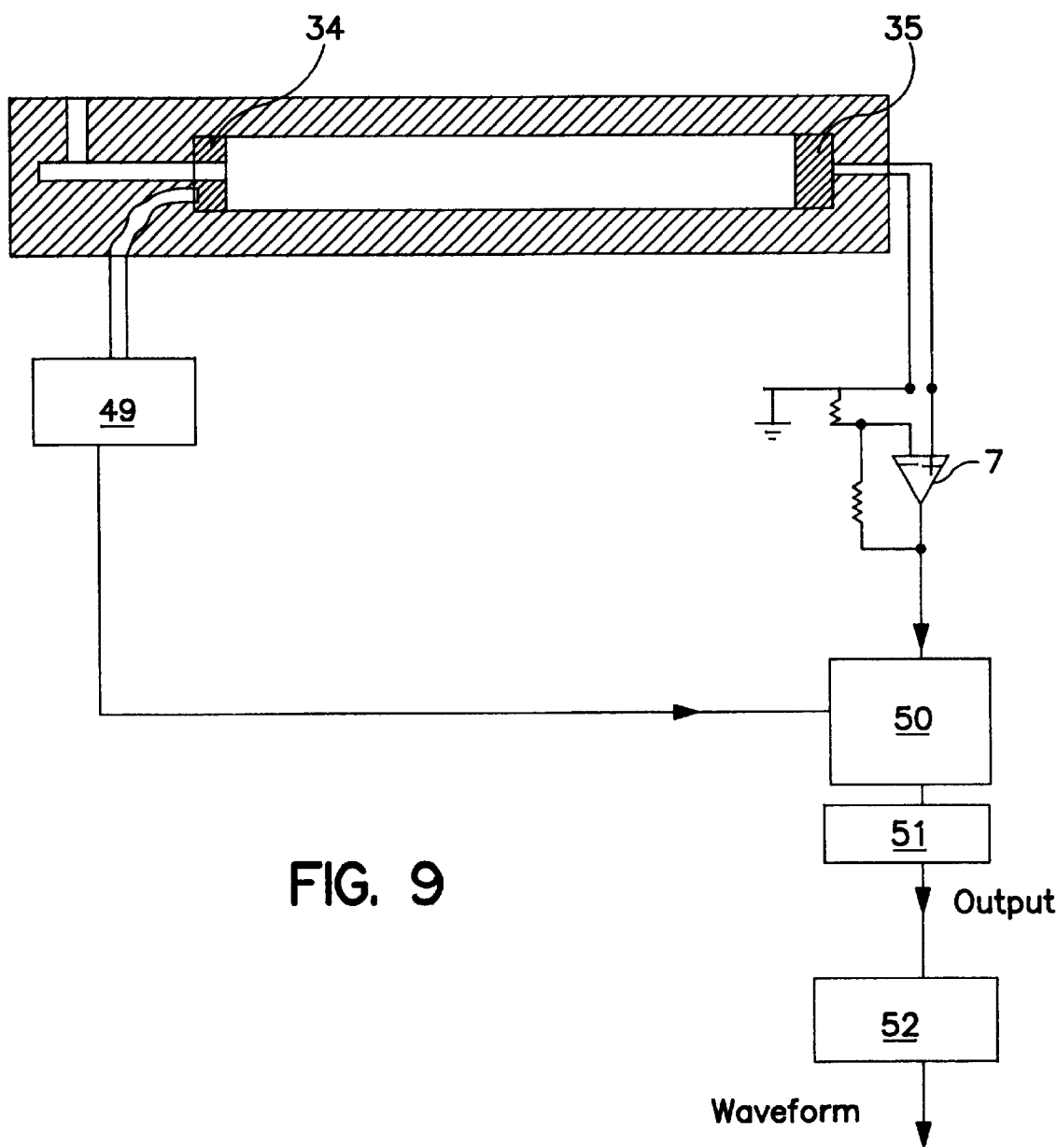
FIG. 9 shows another embodiment of the invention including means for acoustic attenuation in the time domain.

FIG. 9 shows another embodiment of this invention. A pair of ultrasonic sensors are provided, where a high frequency ultrasonic wave is generated at the ultrasonic bender 34 by using an electronic oscillator 49. A signal is received at the receiver 35. Bender 34 and receiver 35 are sonically isolated between the body of the test strip, made, for example, of polyester film. The impedance of liquid sample in the test channel causes an attenuated signal of ultrasonic wave at the receiver side. This attenuated signal is collected and amplified through amplifier 7 in a time window in which multiple circles are collected and fed into a lock-in-phase amplifier 50 together with the original oscillating signal from the source 49. After signals are fed into the lock-in-phase amplifier, a trace signal with high frequency contents (see the left trace shown in FIG. 10) is fed into demodulator 51. Then, an amplitude trace is obtained (see the middle trace shown in FIG. 10). This signal may be described as:

$$S = a \times e^{-bx} \quad (1)$$

Figure 10:
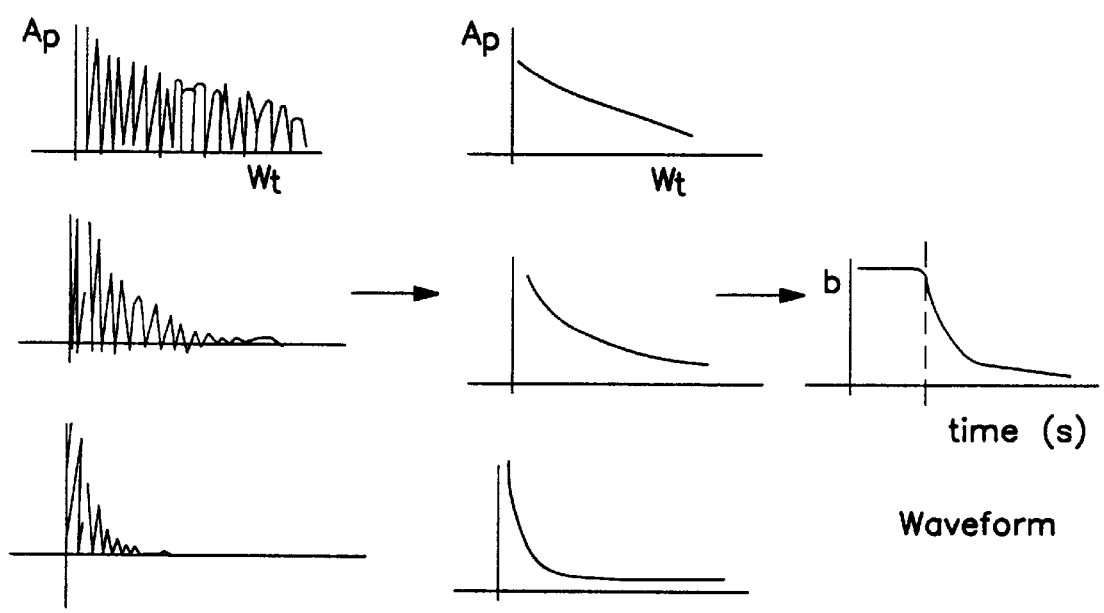
FIG. 10 shows graphs illustrating acoustic attenuation in the time domain.

Through data conversion box 52, parameter b in equation (1) above is converted to the secondary signal shown in the right trace in FIG. 10, as a function of time. As clot formation proceeds (the clot starting point) where polymeric fibrin starts to form (the dotted line in the right trace in FIG. 10), a prothrombin time is defined (in units of seconds).

COMBINATION OF OPTOACOUSTICS AND PIEZO SENSING

Figure 11A:
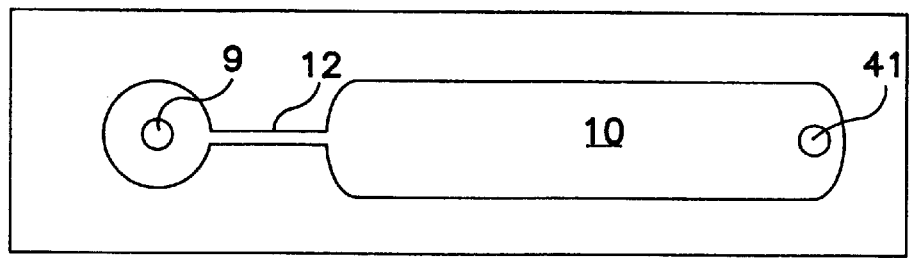
FIGS. 11a and 11b are illustrations of a reaction chamber and a cross-sectional view of an invention embodiment having infrared excitation and piezoelectric detection.
Figure 11B:
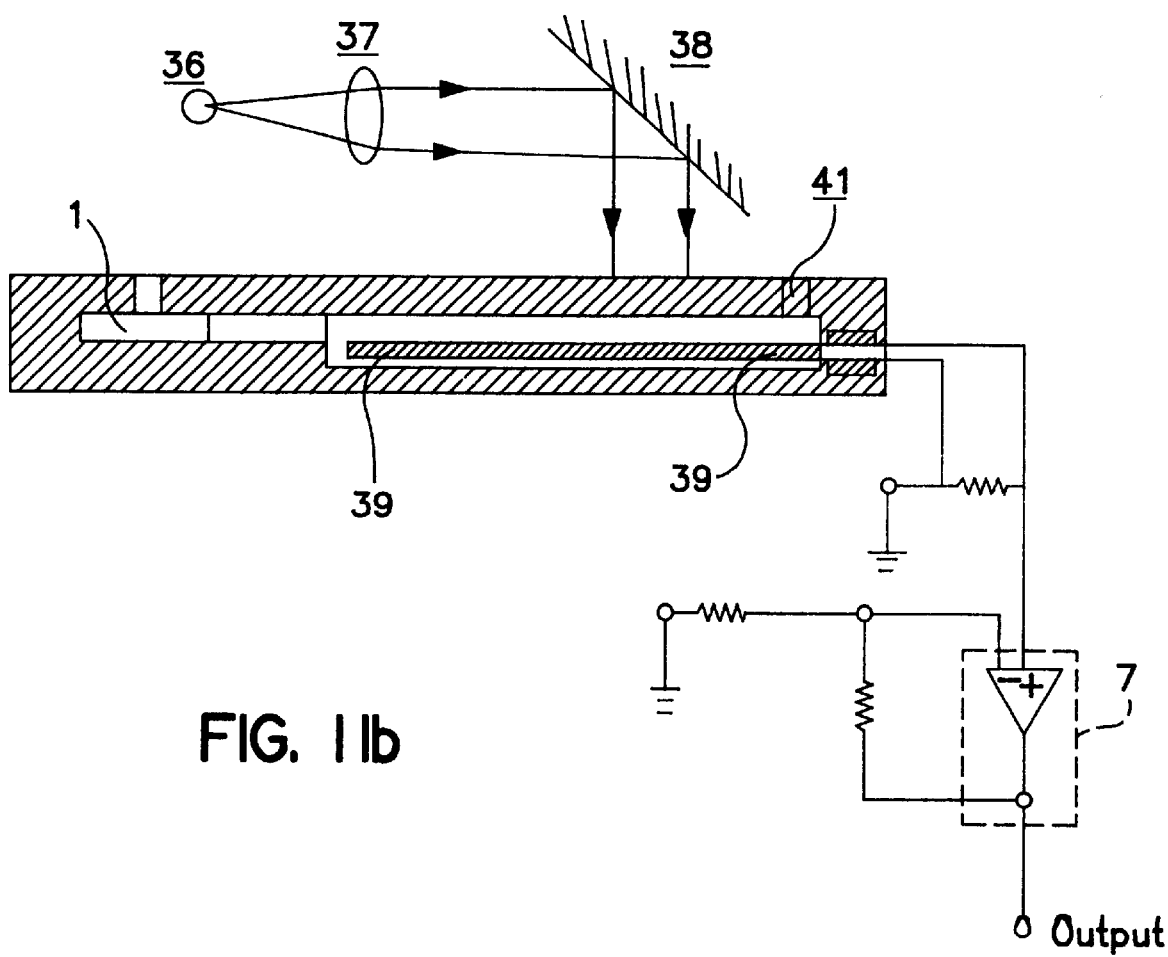

Another embodiment of this invention is shown in FIGS. 11a and 11b where an infrared light source in pulse mode is used for excitation. An infrared light source 36 is focused onto a focus lens 37 and reflected through mirror 38 onto the reaction chamber. A piezo-sensing film is located in the reaction chamber (e.g. at the bottom). The incident light energy leads to periodic heating in the sample media (e.g. body fluid) which is converted to mechanical energy at acoustic frequency at the solid/liquid boundary. Piezoelectric signal is generated from the energy transfer mechanism. Changes in piezoelectric signal occur upon the formation of a clot, and this change indicates the prothrombin time when polymeric fibrin clot formation began.

Figure 12A:
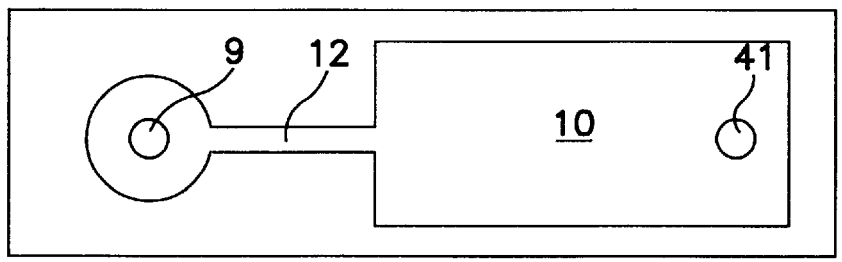
FIGS. 12a and 12b are illustrations of an embodiment of the invention using infrared interferometric piezosensing.
Figure 12B:
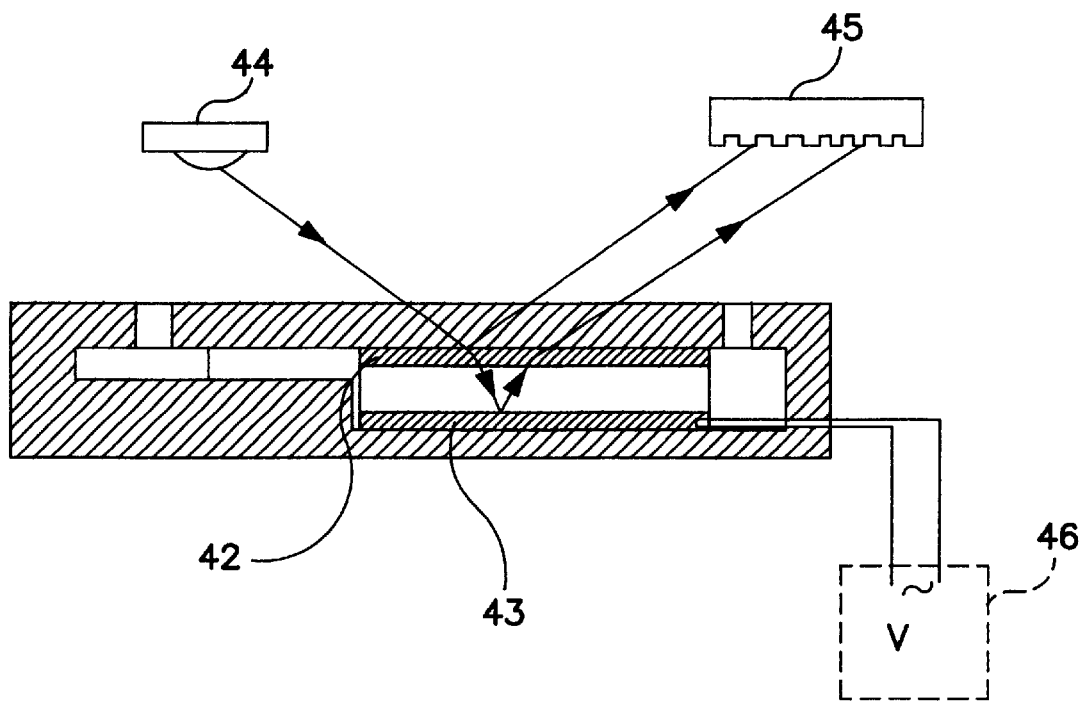

Since piezoelectric sensing can be very sensitive to local temperature variations in the sample vicinity, an optical readout is desired and provides several advantages over other techniques. Also, optical interferometric sensing can offer high sensitivity, accuracy and reproducibility over mechanical sensing. FIGS. 12a and 12b illustrate a simple encapsulated, test strip. FIG. 12a illustrates a sample inlet area 9 where a drop of blood is delivered onto the test strip. Vent 41 provides air venting. After addition of the blood sample (whole blood or plasma), the blood flows into reaction chamber 10 through channel 12 driven by capillary force. As shown in FIG. 12b, inside the transparent top layer of the device is a reflective layer 42 (e.g. an aluminum layer) serving as a mirror (or a fine silicon surface, a magnesium film etc.). A piezoelectric film 43 (e.g. a PVDF film) is disposed at the bottom of the reaction chamber. Incident light generated by light source 44 (e.g. a laser diode or a flash lamp) is incident on the surface of mirror 42 and reflected to signal detector 45 (e.g. a diode array or a photo cell detector or a detector chip, see below for details). At the boundary between the reflective layer and the sample fluid, incident light splits into two beams. One beam is reflected and the other is transmitted into the sample liquid and then onto the piezo film. At the solid-liquid boundary of the piezo film, the light is reflected again back to the detector. These two beams of light are interfered coherently and collected at the signal detector 45. The piezoelectric film vibration is generated by an electric oscillator voltage source 46. The mechanical vibration of the piezo element is translated into the optical signal collected at the detector. Any variations at the piezo element are translated into a change in the intensity of this interferometric modulated light at the light detector. In the reaction chamber where blood sample is mixed with appropriate reagent (e.g. thromboplastin for prothrombin time) piezoelectric vibration will not change until a fibrin clot starts to form. Therefore, the interferometric signal collected at the light detector will indicate the clot formation in a real time scale.

EXAMPLE 3

Referring to FIG. 12a and FIG. 12b, a laser diode is used with a wavelength of 1300 nm in pulse mode at 30 kHz and with a capacity of 50 mw. A diaphragm made of copper is 50 μm thick and used as the acoustic bender which has good thermal diffusion and low modulus of elasticity. The bender is tuned with an oscillator with proper amplitude of about 39 nm. The sensor is working in its light intensity modulation mode. The deflection of the diaphragm is within a quarter of the wavelength and the detected light intensity is in the quasi-linear region in response to changes in the bender deflection. Taking into account the fact that the precision of the detected light corresponds to an amplitude variation of $10^{-10}$ m at the bender surface, a signal-to-noise ratio of 70–80 dB is achieved. By converting the real time signal collected at the detector using high frequency filters, a real-time course of clot formation is obtained. This information is sent to an algorithm block in the device and translated into a clinically significant parameter: prothrombin time in the case of thromboplastin being used as the reagent.

EXAMPLE 4

Another embodiment related to the application of the optoacoustic principle is the use of a Fabry-Perot (FP)

interferometer. Similar to the construction as shown in FIG. 12b, a pair of thin layer mirrors are made and the top mirror is half-transparent while the other is total reflective. (Two spacers are in between.) The bottom mirror is sited on the top of a silicon wafer acting as the acoustic bender in this example. The two mirrors form a Fabry-Perot (FP) interferometer and the incident light is reflected through the two paths and then collected at the detector. The device runs in the wavelength modulation mode where the reflection and transmission of incident light is a function of the wavelength. The wavelength modulation depends on the width of the F-P cavity. The deflection of the quartz element driven by a defined oscillator is a function of viscosity of the liquid under testing (while other parameters of the acoustic bender remain the same). As shown in FIG. 12b the detector 45 is made of three pn-junction photodiodes. The photodiode in the middle is a regular pn-junction while the left and right ones are integrated with two optical FP filters of slightly different thickness. The middle n-p junction serves as an optical reference for the wavelength demodulation and the other two form a virtual cavity due to the height difference of the two F-Ps. The detector performs an optical comparison between the sensor cavity near the silicon wafer with a virtual cavity at the detector surface. Any change in wavelength modulation will be detected at the detector surface. While keeping all instrumental parameters constant, changes in viscosity lead to a change in deflection of the silicon wafer bender which in turn changes the optimal maximum of the light intensity at the interferometer detector. This signal is converted to an electrical signal and fed into an amplifier. A waveform of clot formation is presented and interpreted in terms of prothrombin time (in the case of using thromboplastin as the reagent).

EXAMPLE 5

Figure 13:
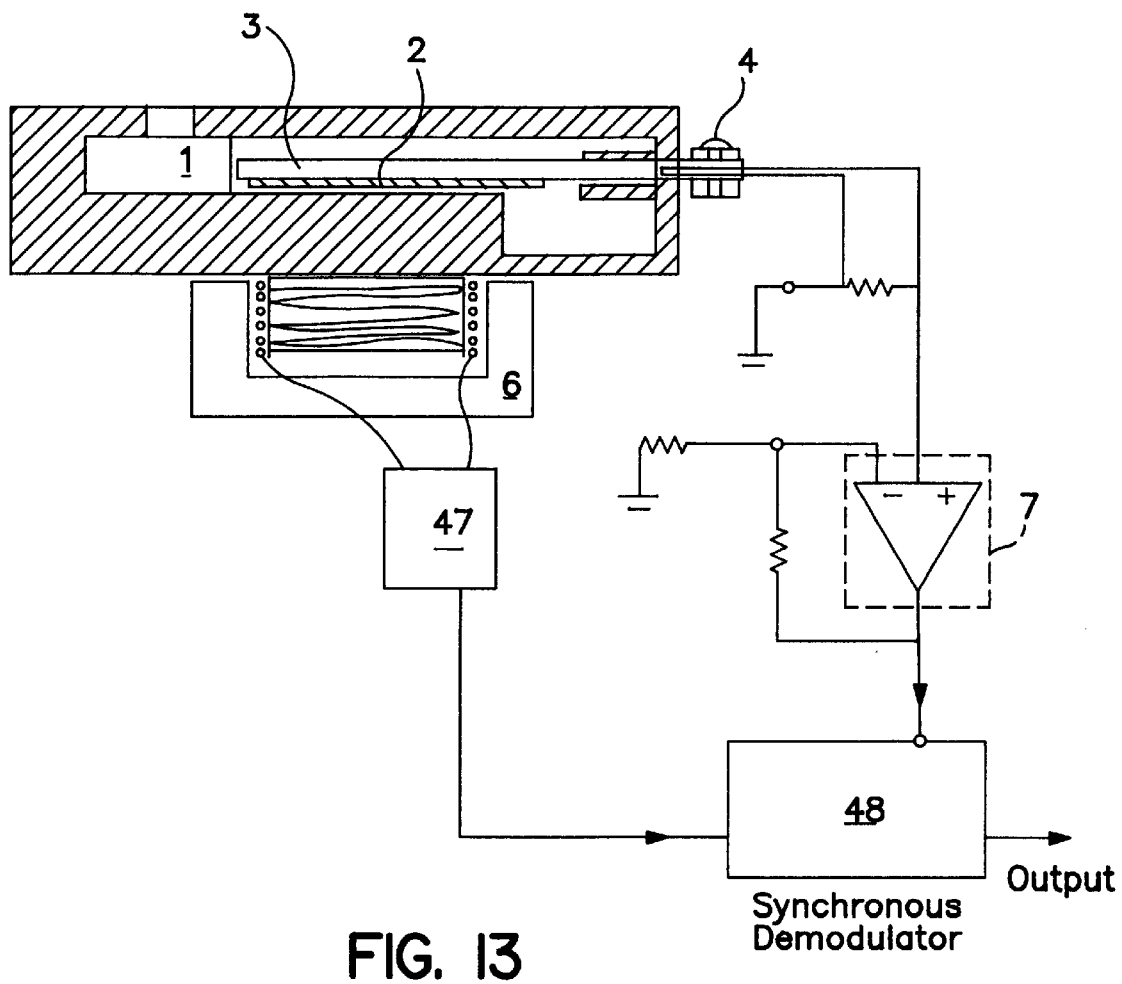
FIG. 13 is an illustration of an embodiment of the invention using a synchronous demodulator.
Figure 14:
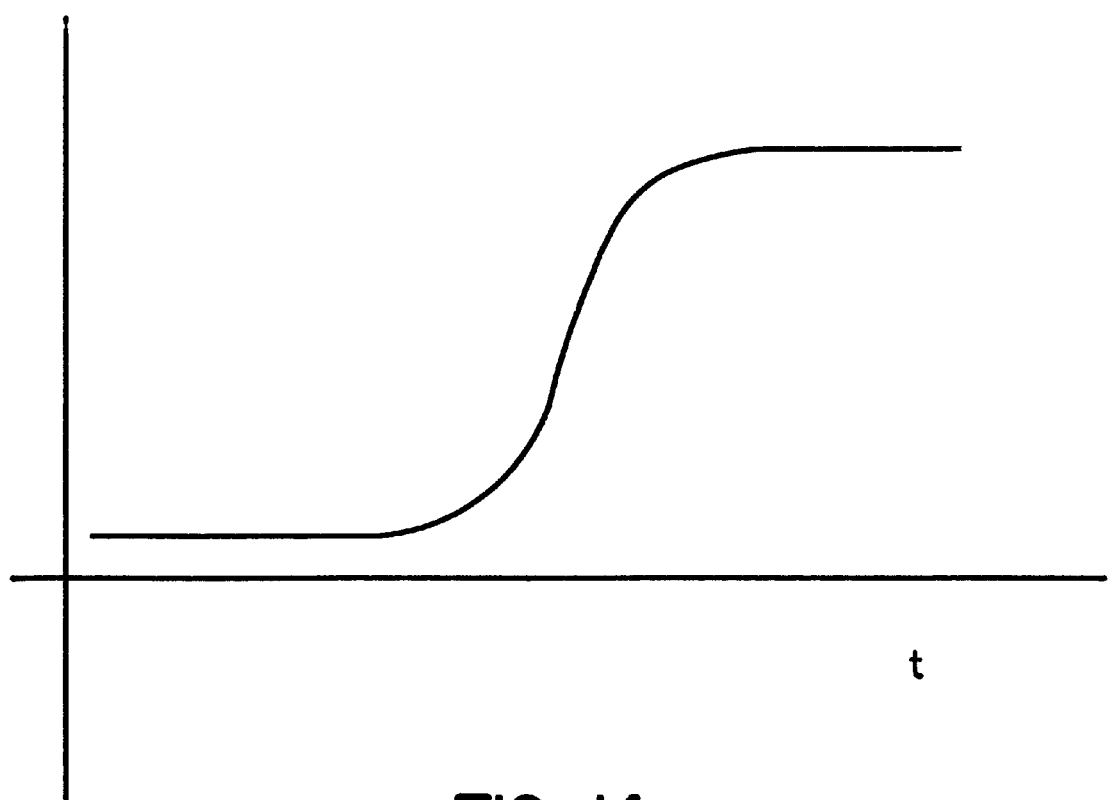
FIG. 14 is a simulated form of a piezosensing waveform using a synchronous demodulator.

Another example of the invention is illustrated in FIG. 13. An electric oscillator 47 generates vibration of a magnetic bender. These oscillations are detected by the piezoelectric sensing film 3 and amplified through piezoelectric amplifier 7 and then fed into a synchronous demodulator 48. The output signal from this synchronous demodulator provides a waveform in the time domain that reflects the true time event of clot formation. A simulated form of the waveform is illustrated in FIG. 14.

EXAMPLE 6

In the device, a piezo element is made of three layers of film. The top and bottom are two layers of PVDF film (each 25 $\mu$m thick) and the middle layer is made of a silicon compression film (200 $\mu$m thick). The piezo element is in contact with liquid sample and located at the bottom of the reaction chamber of the test strip assembly. The piezo film at the bottom is connected to an oscillator and the top piezo film is connected to a piezoelectric circuit and an amplifier. Signal generated from the oscillator is fed into the bottom piezo element that vibrates under the oscillating field. Silicon film is driven by the mechanical stress of the bottom piezo film. Coupled with the compression film the top piezo element experiences mechanical stress and a piezo-electrical signal is generated at the top piezo element and is sent out to a signal amplifier. Both signals from the oscillator and from the piezoelectric amplifier are fed into a synchronous demodulator. As a result of clot formation the viscosity change in the sample liquid induces an acoustic impedance change and results in a change in amplitude of the piezoelectric signal at the detector. After the synchronous demodulator high frequency component is filtered the signal becomes a waveform representing prothrombin time.

It is to be understood that the invention described and illustrated herein is to be taken as a preferred example of the same, and that various changes in the method and apparatus of the invention may be resorted to, without departing from the spirit of the invention or scope of the claims.

We claim:

1. A device for measuring at least one blood coagulation parameter, comprising;
   a housing;
   a sample inlet for the addition of a blood sample to the device;
   a reaction chamber within the housing for the flow or holding of sample within the device;
   an electromagnetic wave generator proximate to said reaction chamber for passing electromagnetic waves through the sample in the reaction chamber; and
   a piezoelectric device for monitoring changes to said electromagnetic waves after passing through said sample so as to detect a changing coagulation parameter of the blood sample.

2. The device of claim 1, further comprising a coagulation reagent for causing coagulation of said blood sample within said reaction chamber.

3. The device of claim 1, further comprising a filter for causing a separation of a first part of the blood sample from a second part of the blood sample.

4. The device of claim 3, wherein said filter comprises an asymmetric membrane.

5. The device of claim 4, wherein said filter further comprises a capillary channel for drawing the blood sample through said asymmetric membrane.

6. The device of claim 4, wherein said asymmetric membrane is a single layer membrane disposed in the proximity of said sample inlet.

7. The device of claim 6, wherein said asymmetric membrane has a thickness of from about 30 to 500 $\mu$m.

8. The device of claim 7, wherein said asymmetric membrane has a thickness of from about 50 to 200 $\mu$m.

9. The device of claim 4, wherein said asymmetric membrane comprises polysulfonate.

10. The device of claim 1, further comprising a heater for maintaining a predetermined temperature of the device when in use.

11. The device of claim 2, further comprising a control chamber.

12. The device of claim 11, wherein said reaction chamber comprises said coagulation reagent, and said control chamber does not.

13. The device of claim 12, wherein said reaction chamber and said control chamber have substantially the same geometry and dimensions.

14. The device of claim 12, further comprising an air reservoir in communication with both said reaction and control chambers.

15. The device of claim 1, wherein said reaction chamber comprises an elongated channel.

16. The device of claim 12, further comprising a first air reservoir in communication with said control chamber.

17. The device of claim 1, wherein said reaction and control chambers are in a concentric spiral formation.

18. The device of claim 17, wherein a piezoelectric device is within or adjacent each chamber, said piezoelectric devices detecting a distance of flow within each chamber.

19. The device of claim 18, further comprising a circuit for comparing signals from said reaction and control chambers.

20. The device of claim 1, further comprising a bender for vibrating within said reaction chamber, said piezoelectric device generating electric signal corresponding to the frequency and amplitude from the bender vibration after passing through the blood sample.

21. The device of claim 20, wherein a changing amplitude is detected at the piezoelectric device during clot formation.

22. The device of claim 20, wherein said bender is a magnetic bender and said electromagnetic wave generator is capable of causing said bender to vibrate.

23. The device of claim 22, wherein said electromagnetic wave generator comprises an AC excitation generator coil and an electromagnet.

24. The device of claim 22, wherein said piezoelectric device is attached at at least one end thereof to an internal wall of said reaction chamber, and said bender is attached to said piezoelectric device.

25. The device of claim 22, further comprising an electronic circuit connected to said piezoelectric device for signal amplification and/or filtering.

26. The device of claim 12, wherein said coagulation reagent is a PT or APTT reagent.

27. The device of claim 1, wherein the piezoelectric device comprises one or more of lead-zirconate-titanate, $BaTiO_3$, lead-magnesium-niobate, or polyvinylidene fluoride.

28. The device of claim 1, wherein said electromagnetic wave generator is an infrared light source, where piezoelectric signal is generated from energy transfer mechanism changes upon formation of a clot.

29. The device of claim 28, further comprising a focusing lens and mirror between said reaction chamber and said infrared light source.

30. The device of claim 28, wherein at least a part of a wall of said housing is substantially transparent for the passage of said infrared energy.

31. The device of claim 1, further comprising a reflective layer proximate to said piezoelectric device.

32. The device of claim 31, wherein said electromagnetic wave generator is a light source whereby part of the incident light for said light source is reflected by said reflective layer to a signal detector, whereby another part of said incident light reflects from said solid liquid boundary of the piezoelectric film and blood sample back to said signal detector to form two beams of light interfered coherently.

33. The device of claim 32, wherein variations of the piezoelectric device are translated into a change in the intensity of the interferometric modulated light.

* * * * *